United States Patent [19]

Nerenberg

[11] 4,446,240
[45] May 1, 1984

[54] PANCREAS SPECIFIC PROTEIN SYSTEMS

[76] Inventor: Samuel T. Nerenberg, 17931 Wellbank La., Huntington Beach, Calif. 92649

[21] Appl. No.: 230,298

[22] Filed: Jan. 30, 1981

[51] Int. Cl.³ ............... G01N 33/56; G01N 33/60; C07G 7/00
[52] U.S. Cl. .................. 436/542; 260/112 R; 436/544; 436/545; 436/804; 436/811
[58] Field of Search ........... 424/1, 12; 213/230 B; 260/112 R, 112 B; 436/543, 544, 545, 804, 811

[56] References Cited
U.S. PATENT DOCUMENTS 3,979,507  9/1976  Baker .................. 424/1.5

OTHER PUBLICATIONS

Nerenberg et al., Clin. Chem., 26 (2) 209–213, (1980).

*Primary Examiner*—Christine M. Nucker
*Attorney, Agent, or Firm*—Fitch, Even, Tabin & Flannery

[57] ABSTRACT

Pancreas specific protein systems, including Pan Ag purified antigen having molecular mass of about $2.25 \times 10^5$ daltons and pancreas specific antibodies to such antigen, and methods for providing and utilizing such antigen and antibodies.

18 Claims, 7 Drawing Figures

PANCREAS SPECIFIC PROTEIN SYSTEMS

The present invention is directed to protein systems having diagnostic medical utility, and more particularly, is directed to pancreas-specific protein systems including pancreas specific antigens and antibody systems useful in immunoassay methods for diagnosis or analysis of pancreatic disease.

Based on the findings that isozymes are leached from damaged tissue or organs into the circulating blood to produce a composite isozyme pattern of that normally found in the blood with that of the (damaged) tissue of origin, the detection and quantitation of isozymes following tissue of organ damage has found utility in the diagnosis of clinical conditions [S. T. Nerenberg, "Electrophoretic Screening Procedures," Lee and Febiger, Philadelphia, 1973]. Unfortunately, isozyme patterns, although characteristic, are not specific: a variety of diseases affecting different tissues may present similar isozyme patterns or the patterns may become too complex to interpret when disease affects multiple organs.

However, in principle, detection and quantitation (e.g., by means of sensitive procedure such as radioimmunoassay) of a tissue or organ specific protein (normally absent or present at low levels in the circulation) leaching into the circulation during a pathological process could be used to specifically pinpoint the tissue of origin in addition to quantitatively gauging the degree of damage. Much experimental evidence supports such an approach. For example, a great variety of organ specific antigens have been isolated from liver [K. H. Meyer Zum Buschenfelde, et al., "Liver Specific Antigens—Purpose and Characterization," Clin. Exp. Immunol., 10: 89, 1972; I. O. Auer, et al., "Studies on Thermostable Liver Specific Antigens," Int. Arch. Allergy, 42: 871, 1972; K. Sugamura, et al., "Purification and Characterization of Human Liver Specific F-Antigen," Clin. Exp. Ummunol., 26: 28, 1976], heart [U. C. Chaturvdi, et al., "Separation and Characterization of Cardiac Antigen Proteins," Clin. Exp. Immunol. 15: 613, 1973; I. Friedman, et al., "Electron Microscopical Studies of the Effect of Antiheart Antibodies and Complement of Beating Heart Cells in Culture," J. Molec. Cell Cardiology, 8: 641, 1976; E. Espinosa, et al., "Antigenic Analysis of Human Heart Tissue—Further Characterization of an Organ Specific Antigen of Heart Tissue," J. Immunol., 106: 611, 1971], thyroid gland [S. Shulman, "Tissue Specificity and Autoimmunity," Springer-Verlag, New York, Chapter 2, 1974], nervous tissue [S. Shulman. Ibid, Chapter 4; F. Milgrom, et al., "Thermostable Ethanolinsoluble Antigens of Brain," J. Immunol., 92: 82, 1964; S. R. Cohen, et al., "A radioimmunoassay for Myelin Basic Protein and its Use for Quantitative Measurements," J. Neurochem, 25: 371, 1975], kidney [H. J. Intorp, "Thermostable Kidney Antigen and its Excretion into Urine," J. Immunol., 100: 1195, 1968], gastrointestinal tract [K. W. Sell, et al., "Organ Specific Membrane Antigens," etc., Brit. J. Exp. Path., 50: 413, 1969; I. Hakkinen, et al., "The Appearance of Blood Group and Organ Specific Antigens in Human Gastric Glycoproteins," Int. Arch. Allergy. Appl. Immunol., 39: 272, 1969], lymphoid cells [D. G. Colley, et al., "Cellular Differentiation in the Thymus—II. Thymus Specific Antigens in Rat Thymus and Peripheral Lymphoid Cells," J. Immunol., 104: 585, 1970; N. Rose, Autoimmune diseases in the Inflammatory Process," Acad. Press, pp. 347-390, 1974], adrenal glands [N. Rose, ibid; F. Milgrom, et al., "Immunological Studies on Adrenal Glands—III. Interspecies Relations of the Thermostable Adrenal Specific Antigens," Immunology, 6: 105, 1963], reproductive organs [S. Shulman, supra; N. Rose, supra]; and other organs of human and animal origin [P. Curzen, "The Antigenicity of Human Placenta," Proc. Royal Soc. Med., 63: 65, 1970; P. D. Mehta, "Comparative Studies of Lens Alpha-Crystallin From Eight Species," Comp. Biochem. Physiol., 38: 637, 1971; T. Aoki, et al., "Analysis of Soluble Anitgens in Guinea Pig Epidermis—II. Physico-Chemical Characterizations of Tissue Specific Antigens", Immunology, 16: 499, 1969]. Moreover, it is known that organ specific antigens are released into the circulation in a number of pathological conditions, i.e., following liver necrosis [Meyer Zum Buschenfelde, et al., supra; D. Doniach, "Auto Immune Aspects of Liver Disease," Brit. Med. Bull., 28: 145, 1972], in renal disease [H. J. Intorp, et al., supra; A. P. Forbes, "Circulating Antibody to Renal Collecting Ducts in Patients with Hepatoma or Renal Cell Carcinoma," Clin. Exp. Immunol. 26: 426, 1976], in multiple sclerosis [S. R. Cohen, "Radioimmunoassay of Myelin Basic Protein in Spinal Fluid—An Index of Active Demyelination," N. Eng. J. Med., 295: 1455, 1976] and thyroiditis [S. Shulman, supra].

In addition to antigens, circulating antibodies to a variety of tissue components have also been detected in a number of pathological conditions. For example, anti-heart antibodies have been detected following surgery and after myocardial infarction [E. V. Hess, et al., "Heart Muscle Antibodies in Rheumatic Fever and Other Diseases," J. Clin. Invest., 43: 886, 1964; W. I. Heine, et al., "Antibodies to Cardiac Tissue in Acute ischemic Heart Disease," Amer. J. Cardiol. 17: 798, 1966; D. T. Golan, et al., "Antiheart Auto-Antibodies in Ischemic Heart Disease Patients," Clin. Exp. Immunol., 26: 86, 1976]. Moreover, antibodies to adrenal gland appear in Addison's disease and anti-thyroid antibodies are detectable in patients with thyroiditis [R. M. Blizzard, "The Incidence of Adrenal and Other Antibodies in the Sera of Patients with Idiopathic Adrenal Insufficiency (Addison's Disease(", Clin. Exp. Immunol., 1: 19, 1967; S. Shulman, supra].

Circulating antibodies to pancreas have also been detected in patients and in dogs with experimentally produced pancreatic necrosis [A. P. Thal, "Isoantibody formation in Chronic Pancreatic Disease", Lancet, 1: 1128, 1959; M. J. Murray, "The Clinical Significance of Circulating Pancreatic Antibodies," Anl. Int. Med., 53: 548, 1960]. Furthermore, antibodies to pancreatic extracts of human or animal origin can be elicited by injecting the latter into rabbits [R. Metzgar, "Human Pancreas—Specific Isoantigens," Nature, 203: 660, 1964; R. S. Metzgar, "Immunologic Studies of Pancreas—Specific Isoantigens, J. Immunol., 93: 176, 1964; A. A. Mihas, "Antigenic Properties of Subcellular Fractions from Canine Pancreas: Development of a Zymogen Membrane Specific Antibody," Proc. Soc. Exp. Biol. Med., 150: 618, 1975] and other animals [R. Metzgar, supra; E. L. Greene, et al., "Two Pancreas 'Tissue Specific' Antigens in Normal Urine, one Being an Esterease," Int. Archs. Allergy Appl. Immunol., 48: 764, 1975]

However, immunological approaches to the etiology, and particularly the diagnosis, of pancreatic disease have received relatively little attention in the art. Early studies with hemagglutination and gel-diffusion techniques have demonstrated the presence of circulating autoantibodies to pancreas in patients with various pancreatic diseases [M. J. Murray, supra]. More recent studies, with immunofluorescence staining procedures, have confirmed some of these observations [R. Lendrum, "Antibodies Reacting With Human Exocrine Pancreas," Gut, 16: 405, 1975]. Although antiserum specific for human pancreas has been produced in rabbits and monkeys, data on the isolation and characterization of pancreas-specific antigens are scant. One pancreas-specific but not species-specific antigen has reportedly been detected and localized in the zymogen granules [A. A. Mihas, supra], and two pancreas-specific antigens recently detected in urine have been partially characterized [E. L. Greene, supra].

The etiological relationship between chronic alcoholism and acute and chronic pancreatitis is still enigmatic, in spite of the long-known association of the two [K. H. Soergel, supra; E. Clark, "Pancreatis in Acute and Chronic Alcoholism," Am. j. Dig. Dis., 9, pp. 428–431, 1942; H. Sarles, "Review: Alcoholism and Pancreatis, Scand. J. Gastroenterol., 6, 193–198, 1971; L. I. Kager, et al., "Alcohol Consumption and Acute Pancreatis in Men," Scand. J. Gastroenterol., 7, 3–38, 1974; W. B. Strum, et al., "Chronic Pancreatis," Ann. Intern. Med., 74, 264–277, 1971] and in spite of prolonged critical and experimental study [L. I. Kager, et al., supra; W. B. Strum, et al., supra; H. Sarles, "Chronic Calcifying Pancreatitis-Chronic Alcoholic Pancreatitis," Gastroenterology, 66, 604–616, 1974; J. E. Trapnell, "Acute Pancreatitis in Great Britain—A Review", Med. Aust. 2, 450–455, 1974]. Clinical recognition of pancreatitis tends to be uncertain [P. B. Lesser, "Differentiation of Pancreatitis from Common Bile Duct Obstruction with Hyperamylasemia," Gastroenterology, 68, 636–641, 1973; R. I. Levine, et al., "Enhancement of Amylase-Creatinine Clearance Ratio in Disorders Other than Acute Pancreatitis," N. Eng. J. Med., 292, 329–332, 1975; E. C. Kafka, et al., "Pancreatic Disease," Postgrad. Med., 57, 140–146, 1975; H. Olsen, "Pancreatitis: A Prospective Clinical Evaluation of 100 Cases and Review of the Literature," Am. J. Dig. Dis., 19, 1077–1090, 1974], there being no completely reliable method of diagnosis short of laparotomy [G. Glaser, "Haemorrhagic and Necrotizing Pancreatitis," Br. J. Surg., 62, 169–176, 1975; P. Lesser, et al., "Diagnosis of Pancreatitis Masked by Hyperlipemia," Ann. Intern. Med., 82, 795–798, 1975; N. G. Graham, "Acute Pancreatitis," Practitioner (London) 214, 763–775, 1974].

An increasingly serious problem presenting itself in Western countries is the association of pancreatitis with chronic alcoholism. The condition is below the level of clinical recognition for 8–10 years, after which time it becomes progressive even with discontinuance of alcohol ingestion. Little is known of the underlying mechanisms affecting the pancreas during this so-called "latent phase" (frequency, rate of progression, etc.). Development of a detection system to identify these latent cases would contribute greatly to the selection and study of these cases and concomitantly to the understanding of the pathophysiology and perhaps to the treatment of these cases. It is worth noting that the ever increasing morbidity and mortality of alcoholic pancreatitis which is now being seen is in part due to the teenage drinking problem now encountered in the U.S. [E. Clark, supra; G. T. Shires, et al., "Pancreatic Trauma in the Pancreas," C. V. Mosby & Co., p. 335, 1973; F. A. Carone, et al., "Acute Pancreatic Lesions in Children Treated with ACTH and Adrenal Steroids," N. Eng. J. Med., 257, 690, 1957; W. H. Hendren, et al., "Pancreatitis in Childhood: Experience with 15 Cases", Arch. Dis. Child., 40, 210, 1965]. There is accordingly a need for improved diagnostic techniques for investigation of this latter group.

Difficulties in conventional diagnosis of pancreatitis stem from long-established dependence on detection of increased activities of amylase (EC 3.2.1.1) and lipase (EC 3.1.1.3) in serum and urine. Unfortunately, slight increases in activities of these enzymes tend to be non-specific [P. B. Lesser, supra; R. Belliard, "Incidence and Significance of Hyperamylasemia in Postoperative Patients," Clin. Res., 19, 386, 1971], whereas marked increases are also present in such conditions as perforated gastrointestinal ulcers, occlusion of mesenteric vessels, obstruction of gangrene of the bowel, and ruptured aortic aneurysms. Moreover, increased values in proved cases of pancreatitis tend to correlate poorly with the severity of the condition. The diagnosis of pancreatic disease has lagged behind that of other organs due, largely, to its relative inaccessibility to direct or indirect examination. Although some advances have been made recently, viz, selective arteriography, selenomethionine scanning, ultrasound, etc., diagnosis frequently defies clinical analysis by even the most astute clinicians. Even so, most of these relatively sophisticated techniques are limited to a few medical centers and, at best, are impractical for routine use for the diagnosis of benign or malignant lesions of this organ. Cancer of the pancreas, now the fourth most common cancer in Americans, is virtually incurable due to late diagnosis and is frequently difficult to diagnose even at the operating table due to the reluctance of surgens to biopsy this organ due to the fear of creating a pancreatic fistula. Pancreatitis is an ever-increasing serious clinical problem in Western culture and is difficult to diagnose due to reliance on the determination of blood and urine amylase and lipase. As indicated, hereinabove, tests for the latter constituents in the blood are known to be nonspecific with the result that surgeons faced with the differential diagnosis of "surgical abdomen" (perforated peptic ulcer, gangrene of small bowel or other clinically dangerous disease) or pancreatitis, may be forced to carry out an exploratory laporatomy to avoid the catastrophic results resulting from making a diagnosis of pancreatitis when an acute surgical abdomen actually exists. In addition to its non-specifiity, elevated blood amylase demonstrates an evanscent character. With these deficiencies in mind, it becomes readily apparent that there is a need for improvement in diagnostic laboratory testing to improve the diagnosis, treatment and investigation of pancreatic diseases. It is also known that certain hereditary diseases such as cystic fibrosis can affect the pancreas, and there is a need for improved testing for distinguishing other diseases of the pancreas from such hereditary diseases affecting the pancreas.

It is readily apparent from the discussion above that a new approach to the laboratory diagnosis of pancreatitis is needed to advance the field. The escape of pancreatic enzymes (amylase and lipase) during a severe attack of pancreatitis implies that more specific, soluble (non-enzymatic) proteins might also escape from damaged acinar cells [B. Antoine, et al., "Pathological Urine Excretion of Tissue Macromolecules (Histuria)," J. Lab. Clin. Med., 71, 101–112, 1968; J. H. Bass, et al., "Tissue Antigens Excreted in Urine Under Normal and Pathological Conditions," Isr. J. Med. Sci., 9, 49–508, 1973]. If an appropriate, pancreas-specific protein could be isolated from the vast numbers of different proteins, peptides and related materials present in the pancreas, and subsequently identified and detected in the blood or tissue samples, a highly specific, sensitive test for damaged pancreatic acinar cells might be provided.

Accordingly, it is an object of the present invention to provide pancreas specific protein systems which may be utilized in the detection or diagnosis of pancreatic disease. It is a further object to provide methods for detection of organ-specific pancreatic antigen in sera or solid tissue samples, which methods are relatively simple, and which may be readily carried out. These and other objects of the present invention will become more apparent from the following detailed description and the accompanying drawings, of which:

Generally, the present invention is directed to a particular pancreas specific protein (hereinafter referred to as "Pan Ag") in purified form and monospecific antibodies to Pan Ag, particularly including antisera for this organ-specific pancreatic antigen (including radioactive or other labelled antisera). The present invention also concerns methods for purification, preparation and utilization of the Pan Ag and antisera therefrom. Various aspects of the present invention are set forth in Nerenberg, et al., "Isolation and Characterization of a Human Pancreas-Specific Protein," *Clinical Chemistry*, Vol. 26, No. 2, pp. 209–213 (February, 1980) and Nerenberg, et al., "Radioimmunoassay for Detection of Latent Chronic Alcoholic Pancreatitis, an Unrecognized Clinical Syndrome," *Clinical Chemistry*, Vol. 26, No. 2, pp. 214–218 (February, 1980), which are incorporated herein by reference.

In accordance with various aspects of the present invention, a cytoplasmic human pancreas-specific protein has been isolated and characterized, and an antiserum specific to this protein has been developed for use in immunoassays. The purified cytoplasmic pancreatic acinar cell protein antigen in accordance with the invention has been isolated from pancreatic extracts. This specific pancreatic antigen has a molecular weight of about $2.25 \times 10^5$ daltons, a carbohydrate content of about 18 percent by weight, and precipitates at between about 245 and about 340 grams per liter of ammonium sulfate saturation (aqueous). The pancreatic antigen retains its antigenic activity in a pH range of from about 2.8 to about 8.5, and migrates electrophoretically in the beta globulin region.

Antisera to the pancreas-specific antigen has been produced and utilized in the purification of the Pan Ag. The antiserum was produced by injecting rabbits with extracts of human pancreas. The rabbit antisera reacted with extracts from several tissues but was rendered specific for pancreas after a series of absorptions [R. S. Metzgar, et al., supra; E. Witebsky, et al., supra; and E. L. Greene, et al., supra]. To eliminate the need for extensive absorptions and simplify the preparation of pancreas-specific antiserum, saline extracts of human pancreas were first fractionated by preparative polyacrylamide gel electrophoresis, and the different fractions were injected into rabbits. Rabbits injected with fraction 4 [FIG. 5] produced on antiserum specific for pancreas after a single absorption with polymerized normal human serum. Specific antiserum was also obtained by injecting rabbits with precipitin arcs prepared by immunoelectrophoresis in agar of a saline extract of human pancreas reacted with rabbit pancreas-specific antiserum. Upon obtaining a relatively large amount of pancreas-specific antiserum a procedure was developed for the purification of a human-pancreas specific antigen involving sequential steps of gel filtration, preparative gel electrophoresis, and immunoaffinity chromatography by a batch technique.

Figure 5:
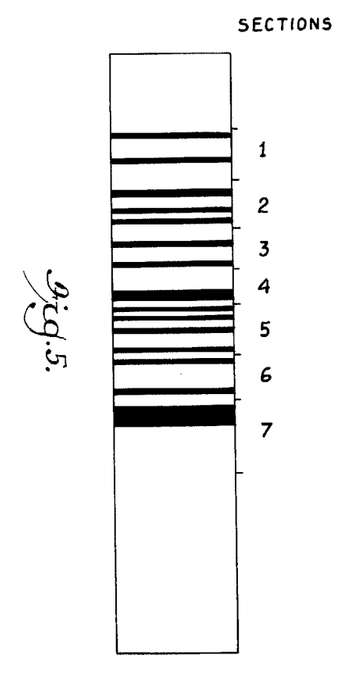
FIG. 5 is a diagram of fractionation of human pancreatic saline extract by preparative polyacrylamide gel electrophoresis.

Saline extracts of human pancreas (prepared as described hereinbelow) fractionated by preparative polyacrylamide gel electrophoresis showed 14 protein bands when the gels were stained with Amido Black (FIG. 5). Rabbit antiserum produced by injecting section 4 of the gel [FIG. 5] appeared specific for pancreas after its absorption with pooled polymerized normal human serum. Additional pancreas-specific antiserum was produced by injecting precipitin arcs as described by Goudie [Goudie, et al., supra]. The absorbed antiserum was tested against saline extracts of various human tissues by radial immunodiffusion. A positive reaction was detected only with human pancreatic extracts, whereas extracts from colon, spleen, liver, kidney, lung, stomach, ovary, heart, uterus, adrenal, thyroid, gall bladder, testicles, prostate, parotid, submaxillary gland and thymus showed no reaction. Extracts of adult human, fetal human, and adult baboon pancreas showed complete antigenic identity, whereas extracts of rat pancreas showed partial identity, as detected by double-gel diffusion. Extracts of rabbit, pig, guinea pig, and dog pancreas did not show any reaction with the rabbit antiserum; futhermore, no reactions were found between the rabbit antiserum and several pancreatic proteins (insulin, amylase, lipase, deoxyribonuclease, alpha-chymotrypsin, elastase, collagenase, carboxypeptidase A and B, leucine aminopeptidase, phospholipase $A_2$, carbonic anhydrase, and gamma-glutamyltransferase), as determined by radial immunodiffusion.

Figure 1:
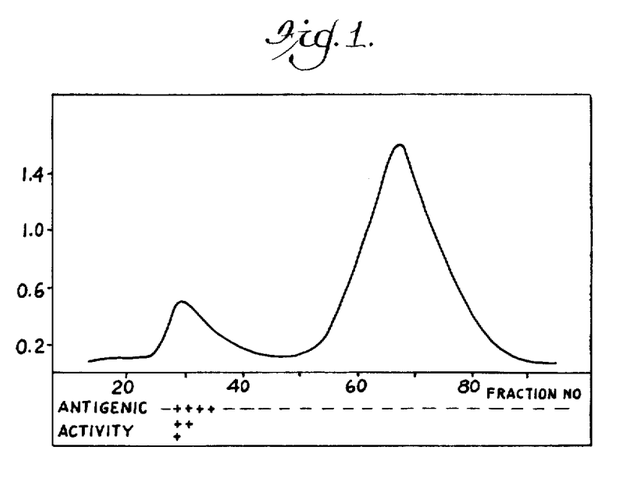
FIG. 1 is a graph representing the antigenic activity of human pancreas extract fractions prepared by gel filtration, with antigenic activity being represented by the designation "+" along the x elution volume axis, and absorbance at 280 μm being represented along the y axis.
Figure 2:
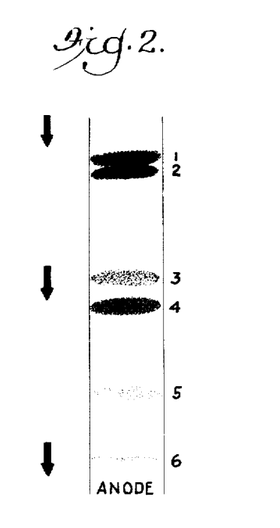
FIG. 2 depicts the fractionation by preparative polyacrylamide gel electrophoresis of antigenically active fraction of pancreatic extract obtained by gel chromatography, with arrows indicating the direction of migration.

In the preparation and purification of the pancreatic antigen, which will be described in more detail hereinbelow, saline extracts of human pancreas were absorbed with CM-Sephadex ($C_{50-120}$; Sigma Chemical Co., St. Louis, Mo. The absorbed proteins were eluted and further fractionated by gel filtration through Sephadex G-200 (Pharmacia Chemical Co., Uppsala, Sweden). The antigenic activity was eluted in the void volume, indicating that the antigen possessed a high relative molecular mass ($M_r$) (FIG. 1). This fraction was further separated by preparative polyacrylamide gel electrophoresis, which yielded six protein bands (FIG. 2). The antigenic activity was located in proteins eluted from Band 3; these proteins were further fractionated by an immunoaffinity batch technique. The eluted protein was antigenically active, as determined by radial immunodiffusion.

Monospecific rabbit antiserum to the isolated, substantially pure pancreatic antigen (Pan Ag) was prepared in accordance with the following general procedure. Saline extracts of human pancreas prepared as described in more detail hereinafter were dialyzed overnight against distilled water, then dialyzed against tris(-hydroxymethyl)methylamine (Tris)-glycine buffer (pH 9.1, 0.04 mol/L) for two days. After centrifuging the dialyzed extract at $27000 \times g$ for 20 minutes, the resulting supernate was collected and fractionated by preparative polyacrylamide gel gradient electrophoresis, as will similarly be explained in more detail. The resulting electrophoretic gels were divided into seven sections (FIG. 5); each section was crushed, homogenized with Freund's complete adjuvant (supplied by Difco Laboratories, Inc., Detroit, Mich.), and injected intradermally into 25 to 30 sites on the backs of each of two rabbits (weight 2 kg.). Rabbits injected with Fraction 4 (FIG. 5) produced an antiserum specific for pancreas after a single absorption with polymerized normal human serum. To boost the titer of the developing antisera, one milliliter aliquots of human pancreatic saline extract containing 20 grams of protein per liter were filtered through a 45-m (average pore size) Millipore filter and the resulting aliquot filtrates were intravenously injected into each of the rabbits three to four weeks later. The rabbits were bled five days after this filtrate injection to prevent development of unwanted, extraneous antibodies. Sera were collected and absorbed with pooled normal human serum that had been polymerized and made insoluble with glutaraldehyde [Nerenberg, et al., *Clinica Chimica Acta* 74, 237–245, 1977]. After mixing 1 mL of rabbit antisera with 1 g of polymer and incubating at 4° C. overnight on a shaker, the supernates were collected and tested by double-gel diffusion and radial immunodiffusion against serum from healthy subjects and extracts of different human tissues.

Additional pancreas-specific antiserum was obtained by injecting rabbits with precipitin arcs, as generally described by Goudie, et al. ["A Simple Method for Producing Antibody Specific to a Single Selected Diffusible Antigen," *Lancet*, ii, 1224–1226, 1966] the arcs were obtained by immunoelectrophoresis of saline extracts of human pancreas, followed by reaction with rabbit antiserum prepared as described above. The arcs were exhaustively washed with saline for one week to remove unreacted proteins, homogenized with equal amounts of complete Freund's adjuvant, and injected intradermally in 25 to 30 sites in rabbits. Each rabbit was "boosted" by intravenous injection of material from two washed precipitin arcs homogenized in saline and bled three and five days later. The booster injections were repeated at weekly intervals for two additional weeks. Antisera were collected as previously described and routinely absorbed with polymerized normal human serum.

As previously indicated, the Pan Ag was purified by absorption of a soluble pancreatic protein fraction obtained as an isotonic solution from specimens of human pancreas obtained fresh at autopsy upon CM Sephadex (a carboxy methyl dextran polymer) fractionation by means of gel chromatography, and electrophoresis. More specifically, the the pancreatic antigen (Pan Ag) was obtained and isolated in accordance with the following procedure: fat, vessels and ducts were removed from fresh human pancreas obtained at autopsy within 12 hours of death, then stored at $-70°$ C. until extracted. All subsequent steps were carried out at 4° C. The frozen tissue was thawed and minced, then suspended in two volumes of 9 g/L NaCl and homogenized in a Waring Blendor at full speed for 1 minute. The homogenate was centrifuged at $27000 \times g$ for 15 minutes, with the resulting supernate being filtered through coarse filter paper. The resulting filtrate was collected, divided into aliquots, and kept at $-70°$ C. The pancreas saline extract was heated to 60° C., immediately cooled to 4° C., and centrifuged at $27000 \times g$ for 20 minutes at 4° C. The pellet was discarded, and the supernate was dialyzed overnight against 0.05 mol/L sodium phosphate buffer (pH 6.0), centrifuged as above, and the resulting supernate filtered through a 0.45 μm average pore size Millipore filter. The filtrate was mixed with CM-Sephadex ($C_{50-120}$; Sigma Chemical Co., St. Louis, Missouri) that had been prewashed with 0.05 mol/L phosphate buffer, pH 6.0 (1 mL of filtrate to 2 g of CM-Sephadex) to provide a suspension which was incubated for 1 hour at room temperature, and subsequently filtered with a Buchner funnel. The Sephadex gel was thoroughly washed with 0.05 mol/L sodium phosphate buffer (pH 6.0), resuspended in 0.05 mol/L sodium phosphate buffer containing 1 mol of sodium chloride per liter (also pH 6.0) for 1 hour at room temperature and filtered. The resulting filtrate was dialyzed against 0.05 mol/L sodium phosphate buffer (pH 7.4) concentrated under pressure in an Amicon filter unit (Model No. 402; Amicon Corporaton, Lexington, Massachusetts), and fractionated by gel chromatography. The gel chromatography purification step was carried out by gel filtration through Sephadex G-200, a gel which selectively absorbs lower molecular weight maerials (e.g., less than 200,000 molecular weight, while passing through higher molecular weight materials in its void volume. In this regard, the filtrates were applied to a $75 \times 2.5$ cm (i.d.) Sephadex G-200 (Pharmacia, Uppsala, Sweden) column and eluted with 0.05 mol/L sodium phosphate buffer (pH 7.4) at a flow rate of 24 mL/h; 3-mL fractions were collected. Fractions containing antigenic activity, as determined by radial immunodiffusion, were pooled and subjected to preparative polyacrylamide gel electrophoresis, as will now be described in more detail.

Preparative electrophoresis was carried out on a $35 \times 4.5$ cm (i.d.) column of 50 g of polyacrylamide gel per liter of 0.04 mol/L glycine buffer (pH 9.2), of the type described in my U.S. Pat. No. 3,640,813. 5-mL samples containing 30 g of protein per liter were applied to the gel and electrophoresed at 200 V and 50 mA for 18 hours at 4° C. After staining a longitudinal slice of the gel with 0.01 mol/L Amido Black stain in 5 mL/L acetic acid to localize the protein bands. The proteins were eluted from the gel with phosphate-buffered saline and the antigenically active protein band 3 of FIG. 2 was further fractionated by immunoaffinity chromatography in accordance with the following procedure.

Rabbit pancreas-specific antiserum (prepared as described hereinbelow) was polymerized with glutaraldehyde at pH 5.5 to form an insoluble immunoabsorbant. The insoluble immunoabsorbent thus provided was then incubated at 4° C. overnight with the antigenically active protein obtained by preparative polyacrylamide gel electrophoresis in the proportion of 1 gram of polymer to 1 mL of eluted protein solution. This resulting suspension was then centrifuged for 5 minutes at 6000×g at 4° C. The resulting pellet of immunoabsorbent provided by centrifugation was washed several times with 0.1 mol/L phosphate-buffered saline, pH 7.4. The antigen was eluted with 0.1 mol/L glycine HCl buffer, pH 2.8. The eluent was immediately brought to pH 7.2–7.4 with solid sodium bicarbonate and then dialyzed against 0.01 mol/L sodium phosphate buffer, pH 7.0. The purity of this resulting antigen (Pan Ag) was examined by polyacrylamide disc gel electrophoresis. In this regard, samples containing 10 to 50 μg. of purified pancreatic antigen were subjected to polyacrylamide disc gel electrophoresis in gels containing 75 grams of polyacrylamide per liter of buffer [B. J. Davis, "Disc Electrophoresis—II. Method and Application to Human Serum Proteins 'gel electrophoresis'", Ann. N.Y. Acad. Sci., 121, 404–427, 1964]. After electrophoresis, gels were stained for protein with Coomassie Blue. Only one band was detected after staining with Coomassie Blue for protein, indicating a substantially pure Pan Ag protein antigen. Further characterization of the Pan Ag antigen was carried out as follows. The purified Pan Ag antigen contained 180 mg of carbohydrate per gram, as determined by the phenol-sulfuric acid method [R. G. Spiro, "Analysis of Sugars Found in Glycoproteins. In Methods in Enzymology," 8, Academic Press, New York, N.Y., pp. 3–26, 1966], and precipitated at between 245.64 and 340.2 g/L ammonium sulfate saturation. The antigenic activity was not affected by heating up to 60° C. for as long as 1 minute or by storage for one year at −70° C.; moreover, it was not affected in the pH range of 2.8 to 8.5 but was destroyed at pH 2.5. After human pancreatic antigen obtained by preparative electrophoresis had been incubated with various enzymes at room temperature for 24 hours, it was tested for antigenic activity by radial immunodiffusion. Enzyme-treated and untreated preparations were analyzed simultaneously. The antigen (150 ng in phosphate-buffered saline) was treated with the following enzymes (all from Sigma); 100 units of *Vibrio cholerae* neuraminidase (EC3.2.1.18) in 0.1 mol/L maleate buffer (pH 6.4) containing 20 mmol of $CaCl_2$ per liter; 100 U of deoxyribonuclease I (EC 3.1.4.5) in 0.1 mol/L acetate buffer (pH 5.6) containing 5 mmol of $MgSO_4$ per liter; 70 U of ribonuclease (EC 3.1.4.22) in 0.1 mol/L acetate buffer (pH 5.6); and 10 ng of trypsin (EC 3.4.21.4) in phosphate-buffered saline. The antigenic activity was destroyed by extraction with 0.25 mol/L perchloric acid or by incubation of the antigen with trypsin and neuraminidase. Destruction of the antigenic activity by incubation with trypsin or neuraminidase, indicates that the carbohydrate moiety is associated with, or is part of, the antigenic site. On the other hand, the antigenic activity was not affected by incubation with deoxyribonuclease or ribonuclease. When subjected to immunoelectrophoresis in agar, the antigen appeared in the B-globulin region.

Figure 3:
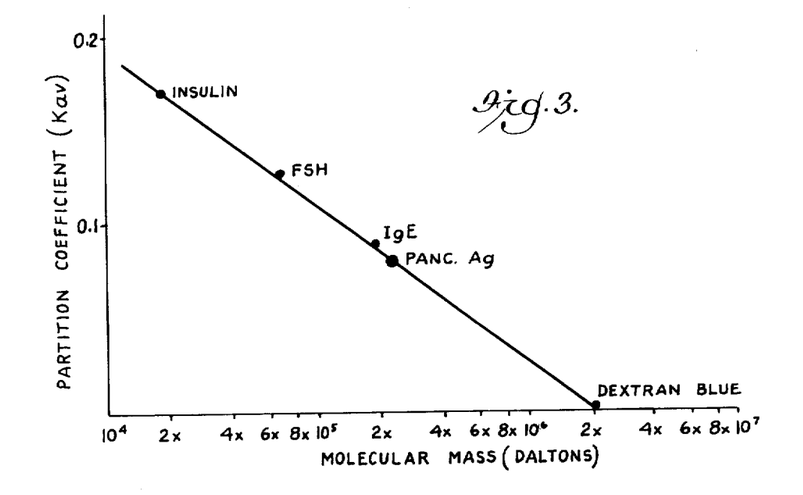
FIG. 3 is a graph illustrating the relative molecular mass of acinar organ specific pancreatic antigen in accordance with the present invention, as compared to reference proteins of known molecular weight.
Figure 4:
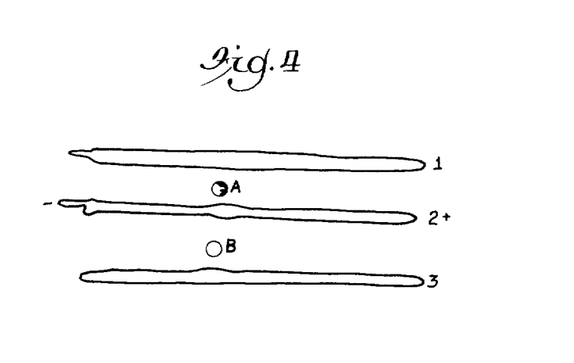
FIG. 4 depicts the immunoelectrophoresis of normal human serum (at B) in comparison with immunoelectrophoresis of human pancreas extract (at A), troughs labelled 1, 2 and 3 contain rabbit antiserum to human pancreatic antigen Pan Ag.

The molecular mass of the purified Pan Ag was determined by gel filtration through acrylamide gel. In this regard, the purified pancreatic antigen was filtered through a 100×0.9 cm (i.d.) column of an acrylamide gel, Biogel A-1.5 m (50–100 mesh; Bio-Rad Lab, Richmond, California) equilibrated with 0.1 mol/L sodium phosphate buffer (pH 7.4) containing 10 mL of 10 g/L bovine serum albumin solution. Highly purified preparations of $^{125}I$-labeled IgE (Pharmacia), follitropin (Amersham Corp., Arlington Heights, Illinois), insulin (Med Vak, Inc., Columbia, Maryland), carcinoembryonic antigen (Hoffman-LaRoche, Nutley, N.J.), and unlabeled blue dextran (Pharmacia) were used as reference markers. The proteins were loaded on the column and eluted with 0.1 mol/L phosphate buffer, pH 7.4, at a rate of 0.75 mL/min. 0.5 mL fractions were collected and the presence of proteins was determined by measuring their radioactivity and their absorption of 280 nm. The partition coefficient [Kav=(total bed volume−void volume)/(total bed volume−void volume)/(total bed volume−sample elution volume)] was plotted for the pancreatic antigen and the "marker proteins" vs molecular mass, as shown in FIG. 3. The antigen appeared as a single, symmetrical peak with a mass of $2.25 \times 10^5$ daltons, determined by comparison with the reference proteins.

The pancreatic antigen was also subjected to various immunoassay techniques specifically including double-gel diffusion [O. Ouchterlony, "In Vitro Method for Testing the Toxin Producing Capacity of Diphtheria Bacteria" Acta Pathol. Microbiol. Scand. 25, 186–191, 1948], radial immunodiffusion [G. Mancini, et al., "Immunochemical quantitation of Antigens by Simple Radial Immunodiffusion", Immunochemistry, 2, 235–254, 1965], and immunoelectrophoresis [S. T. Nerenberg, "Electrophoretic Screening Procedures," Lea & Febiger, Philadelphia, PA, 1973] in agarose gels (10 g/L) in a 0.05 mol/L veronal buffer, pH 8.6.

Immunofluorescent staining techniques were utilized to stain Pan Ag in pancreas tissue samples. Fresh rat pancreas was frozen by sudden immersion into isopentane cooled in liquid nitrogen. Cryostate sections 6-μm thick were fixed in ethanol (950 ml/L) for 5 minutes at room temperature, then rinsed for 10 minutes in phosphate-buffered saline. The sections were incubated with 50 l of rabbit antiserum for 45 minutes in a moist chamber at room temperature; then the slides were rinsed for 30 minutes in phosphate-buffered saline. Next, two drops of a mixture of fluorescein isothiocyanate-conjugated IgG fraction of goat-antirabbit IgG (Cappel Lab., Cochranville, Pa.) and rhodamine (prepared by mixing 1 mL of 10-fold diluted fluoresceinated goat antirabbit serum and 10 μL of 10 g/L rhodamine to the sections) were added and the incubation was continued in a dark, moist chamber at room temperature for 30 minutes. The sections were then rinsed with phosphate-buffered saline for 30 minutes and mounted with buffered glycerol. Normal rabbit serum was used as a negative control. This procedure reveals the cytoplasmic location of the Pan Ag. The antigen appears to be homogeneously distributed in the cytoplasm of rat pancreatic acinar cells, as detected by immunofluorescent staining (FIG. 6); human pancreas showed a similar staining pattern, but the cell morphology was considerably altered by autolysis.

The existence of pancreas-specific antigens has been indicated in a number of reports [R. S. Metzgar, supra; E. Witebsky, et al., supra; A. A. Mihas, et al., supra; E. L. Greene, et al., supra; N. R. Rose, et al., "Studies on Organ Specificity—XI. Isoantigens of Rabbit Pancreas," J. Immunol. 85, 575–587, 1960]. Although these antigens have not been fully characterized, their physical characteristics seem to differ from those of the pancreatic antigen Pan Ag isolated in accordance with the present invention.

Having isolated and purified the previously described organ specific acinar pancreatic antigen, Pan Ag, a radioimmunoassay for the quantitative determination of the pancreatic antigen using $^{125}$I-labeled, purified antigen and rabbit pancreas-specific antiserum was developed to determine whether the pancreas-specific antigen could be shed into the circulation as a consequence of a pathological process in that organ.

As previously described, the pancreatic antigen Pan Ag may be used to raise monospecific antibody in appropriate animals such as rabbits. This antiserum, which may be shown by radial immunodiffusion and immunoelectrophoresis to be organ-specific but not species-specific may be incorporated into a radioimmunoassay (RIA) procedure. Using the RIA, it has been demonstrated that the pancreatic antigen (Pan Ag) is present in extracts of the head, body, and tail of the pancreas, and by using the indirect fluorescence antibody technique, it has been further discovered that this antigen is detectable only in the cytoplasm of pancreatic acinar cells. The RIA was then used to detect and quantify pancreatic antigen in blood specimens from two control populations: normal laboratory personnel and supposedly normal blood donors (see Table 1 hereinbelow). In addition, blood samples were collected from two experimental groups: patients admitted to an alcoholic detoxification center at the University of Illinois Hospital while acutely intoxicated (see Table 2 hereinbelow), and detoxified alcoholic patients who had recovered from an acute alcoholic bout and had abstained from ingestion of ethanol for three to six weeks while under care and survellance at an alcoholic treatment center (see Table 3 hereinbelow).

Figure 6:
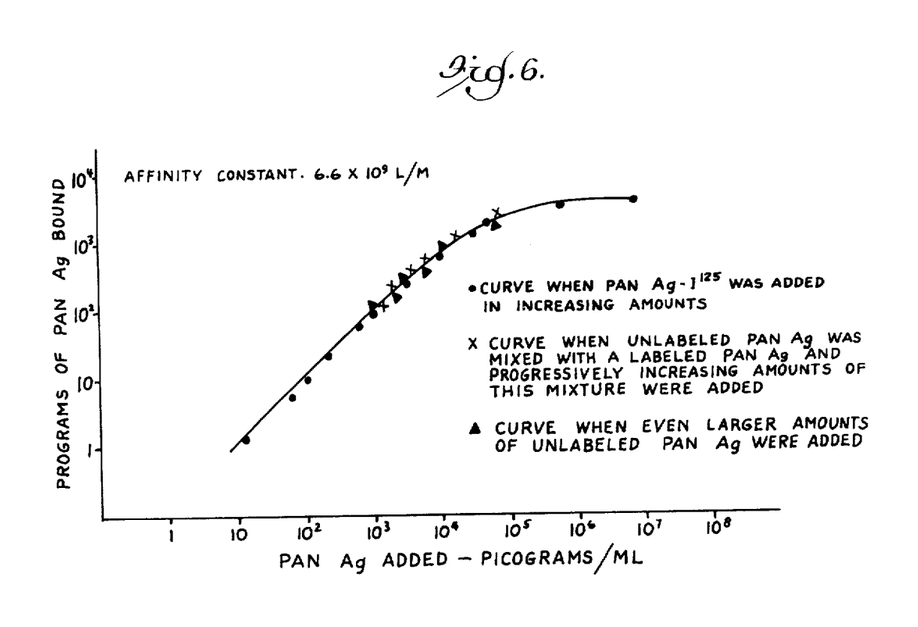
FIG. 6 is a saturation curve for anti-pancreatic antibody against human pancreatic antigen.

The radioimmunoassay procedure was developed as follows. Purified pancreatic antigen was used to prepare antigen standards. The protein content of the concentrated purified antigen was determined by ultraviolet spectrophotometry at 215-225 nm [W. J. Wadell, "A Simple Ultraviolet Spectrophotometric Method for the Determination of Protein," J. Lab. Clin. Med., 48, 311-314, 1966], after which the antigen solution was diluted to 250 micrograms per liter to form a stock standard solution and stored at −70° C. until thawed for use. Working standards of 5, 10, 25, 50, 75 and 90 µg/L were prepared by dilution and stored at −10° C. The Chloramine-T method of Hunter and Greenwood ["Preparation of Iodine-131 Labeled Human Growth Hormone of High Specific Activity," Nature, 194, 495-496, 1962] was used to label the purified pancreatic protein with $^{125}$I. Free $^{125}$I was separated from the tagged protein by gel filtration on a Sephadex G-200 column. The first peak, which contained the labeled protein, was collected and dialyzed overnight in the cold, with several changes of 0.1 mol/L phosphate buffer, pH 7.0, as the dialysate. Damage to the protein was determined during the radioactive labeling by progressive addition of radiolabeled antigen to aliquots of antiserum, to provide a saturation curve for the antibody (FIG. 6). To assess its reactivity, the tagged material was then displaced with progressively increasing amounts of cold antigen [S. T. Nerenberg, et al., "Radioimmunoassay for Ig classes G, A, M, D and E in Spinal Fluids: Normal Values of Different Age Groups," J. Lab. Clin. Med., 86, 887-898, 1975]. Stock antisera used for the assay were stored at −70° C. Other working reagents were stored at −10° C. and were used within six months of storage. Pooled normal human serum and pancreatic extract stored at −70° C. were used as controls.

Working dilutions of antiserum were made at the time of assay. Of the various buffer systems studied, 0.1 mol/L phosphate buffer (pH 7.4 and containing 1 g of EDTA per liter; mix 38 mL of 68 g/L KH$_2$PO$_4$ solution with 162 mL of 87 g/L K$_2$HPO$_4$ solution and dilute to 1 L with distilled water containing 1 g of disodium ethylenediaminetetraacetate (EDTA) per liter.) at an incubation temperature of 50° C. for 1 hour gave the best results. An assay buffer, normal rabbit serum, 10 ml mixed with 500 ml of phosphate-EDTA buffer, was also used in these procedures. Sensitivity of the assay was greatly increased by the sequential saturation technique [A. Zettner, "Principles of Competitive Binding Assay (saturation analysis). Equilibrium Techniques", Clin. Chem., 19, 669-705, 1973]: first incubate the antigen (standard or sample) with aliquots of antibody for 15 minutes at 50° C., then add tracer antigen and extend the incubation period to 1 hour.

To separate bound from free pancreatic antigen, a double-antibody procedure was utilized involving precipitation of the complex with goat antirabbit antiserum. Addition of the second antibody utilized an additional 2 hour of incubation time at 50° C. to precipitate the complex quantitatively. The precipitate was then separated by centrifugation for 15 minutes at 2000×g. At least two washings of the precipitate (2 mL of buffer for each wash) were necessary to free completely the unreacted tracer from the pellet. Radioactivity was counted in a Searle Model A 1185 gamma counter. After optimizing reaction conditions, a standard curve was prepared over a range of 0 to 90 µg/L (FIG. 8). Unknown specimens, controls, standards and blanks were run in duplicate.

Inter- and intra-assay precision were judged by assaying with controls at low, normal and high concentrations (Table 4, hereinbelow). As an indication of accuracy, a stock high control was used to evaluate recovery and parallelism. To assess specifity, the RIA was performed with a tissue panel consisting of extracts from other body organs. Sensitivity was determined as the minimum dose that could be distinguished from the zero dose. For clinical correlation, a normal range was first established from blood samples donated by a known non-alcoholic population, which was then compared with values of samples from patients with high amylase (clinically diagnosed acute pancreatitis) for clinical evaluation.

Serum specimens from all groups were assayed for amylase. In addition, specimens were assayed from the acutely intoxicated group for serum lipase (see Table 2 hereinbelow).

The method of Caraway ["Microchemical Methods for Blood Anaysis" C. C. Thomas Co., Springfield, IL, pp. 98-100, 1960] and a commercial kit (cat. no. 821; Princeton Biomedix, Inc., Princeton, New Jersey 08540) was used to determine amylase and lipase activities, respectively, in serum.

The iodination efficiency after gel filtration was between 85 and 90%. The specific activity, determined by trichloroacetic acid precipitation, was 18 Ci/g. The active peak contained 80% of the antigenic activity, and contents of test tubes containing this material were pooled for use in the assay. The other peak, which contained no detectable antigenic activity, was presumed to be free iodine.

Molecular mass, as estimated by gel filtration, was 225,000 daltons. The affinity constant, as calculated by Scatchard plot [G. Scatchard, "The Attractions of Protein for Small Molecules and Ions," Ann. N.Y. Acad. Sci., 51, 660-672, 1949] and saturation analysis (FIG. 6) was $6.6 \times 10^9$ L/mol. Interassay and intra-assay variations (see Table 4 hereinbelow) did not exceed two standard deviations (2 SD). When control values exceeded target values by more than 2 SD, new stock reagents were substituted that had been stored at $-70°$ C. and the assay was restandardized to maintain deviations at less than 2 SD. In analytical recovery experiments, more than 95% of added, unlabeled pancreatic antigen was recovered. Sensitivity of the assay was 1 microgram per liter.

Specifity of the pancreatic antigen for its homologous antibody was validated by the principle of sequential saturation [A. Zettner, supra], i.e., relatively high displacement (85%) of $^{125}$I-labeled antigen from monospecific, homologous antibody (in the form of an immunoadsorbent) by diluted extracts of pancreas, and very low displacement (0-5%) by the following fluids and tissue extracts: serum from apparently healthy subjects, adrenal, bone marrow, colon, esophagus, gall bladder, heart, kidney, liver, lung, ovary, small intestine, spleen, stomach, testicle and thyroid.

As previously indicated, cross reactivity of the homologous antibody was also checked with other pancreatic proteins; insulin, amylase, lipase, elastase (EC 3.4.21.11), carboxypeptidase A (EC3.4.17.1), carboxypeptidase B (EC 3.4.17.2), collagenase (EC 3.4.24.3), leucine aminopeptidase (EC 3.4.11.1), phospholipase A2 (EC 3.1.1.4), carbonic anhydrase (EC 4.1.1.2) and gamma-glutamyltransferase (EC 2.3.2.2). All failed to react, i.e., none displaced the tracer antigen.

Figure 7:
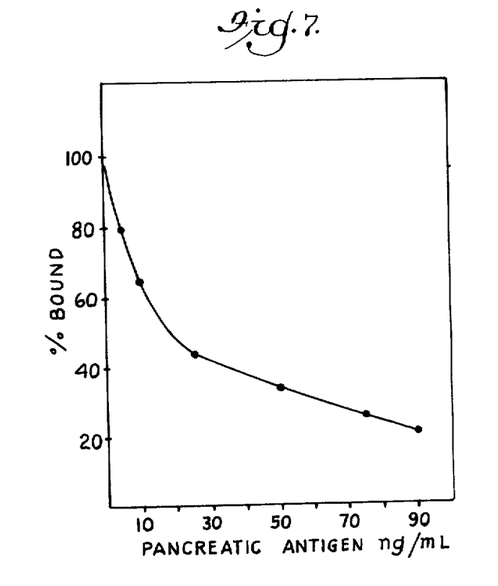
FIG. 7 is a standard curve for radioimmunoassay for human pancreatic antigens over a range of 0 to 90 micrograms per liter.

The derived standard curve for pancreatic antigen (FIG. 7) was used to obtain values for the normal population: 2.1 (SD 1.7) microgram per liter. Using 2 SD to define the normal range (95% confidence limits), a normal range was established as 0 to 5.5. microgram per liter, and 6 microgram per liter was accordingly arbitrarily chosen by rounding upwards as a cutoff point for the normal population.

Anaysis of the control group for pancratic antigen showed that a single sample from the population of laboratory personnel fell within the abnormal range (as shown in Table 1).:

TABLE 1

Pancreatic Antigen (Pan) Concentrations and Amylase Activities in Serum from 32 Blood Donors and 12 Lab Personnel[a]

| Blood Donors | | | | Lab Personnel | |
|---|---|---|---|---|---|
| Pan, μg/L | Amylase, U/L | Pan, μg/L | Amylase, U/L | Pan, μg/L | Amylase, U/L |
| 0.0 | 1680 | 6.0 | 1150 | 2.0 | 1350 |
| 2.5 | 1550 | 0.0 | 1230 | 5.0 | 800 |
| 5.0 | 2030 | 0.0 | 1570 | 3.0 | 660 |
| 2.5 | 2860 | 0.0 | 1530 | 3.0 | 810 |
| 2.0 | 1670 | 1.0 | 1700 | 1.0 | 810 |
| 2.0 | 1550 | 0.0 | 1460 | 2.5 | 820 |
| 5.0 | 930 | 1.0 | 1470 | 7.0[b] | 850 |
| 4.0 | 1880 | 0.0 | 1570 | 4.0 | 860 |
| 3.0 | 1950 | 0.0 | 2140 | 3.0 | 930 |
| 2.0 | 1540 | 2.0 | 1720 | 2.0 | 870 |
| 2.5 | 1490 | 0.0 | 1730 | 2.5 | 1320 |
| 0.0 | 1310 | 0.0 | 1560 | 1.0 | 900 |
| 2.5 | 1230 | 2.0 | 2040 | | |
| 6.0 | 2120 | 2.5 | 1820 | | |
| 15.0 | 1930 | 0.5 | 2040 | | |
| 1.0 | 1510 | 0.0 | 1880 | | |

[a]Pancreatic antigen: mean 2.1 micrograms per liter (SD, 1.7); amylase: mean 1473 U/L (SD, 473).
[b]This individual admitted to chronic ingestion of six bottles of beer per day for six to seven years.

The mean values for serum amylase and pancreatic antigen for the control group were 1473 U/L and 2.1 micrograms per liter, respectively. The amount of antigen detected in the control group followed a skewed distribution.

Experimental Group

Results for 15 of the 85 acutely intoxicated alcoholics are given in the following Table 2, to indicate typical values:

TABLE 2

Pancreatic Antigen and Enzymes in Sera of 15 University of Illinois Alcoholic Patients

| Pancreatic antigen, μg/L | U/L | |
|---|---|---|
| | Amylase | Lipase |
| 5.0 | 1200 | 1200 |
| 4.0 | 790 | 1000 |
| 10.0 | 1030 | 800 |
| 3.0 | 890 | 2000 |
| 2.0 | 1020 | 500 |
| 4.5 | 1380 | 500 |
| 9.0 | 900 | 900 |
| 12.0 | 890 | 40 |
| 10.0 | 2010 | 1000 |
| 10.0 | 1140 | 1100 |
| 4.0 | 990 | 500 |
| 9.0 | 600 | 1300 |
| 3.0 | 1130 | 1300 |
| 0.0 | 1160 | 800 |
| 10.0 | 1330 | 1000 |

The mean value of pancreatic antigen for this group was 6.7 micrograms per liter; 42% (36 cases) had values exceeding 6.0 micrograms per liter (range 7-12.5), 27% (23 cases) had values from 7.5 to 10 micrograms per liter and 6% (5 cases) had values exceeding 10 micrograms per liter (range 11-12.5). The mean values for serum amylase and lipase on these 85 cases were 1000 and 900 U/L, respectively.

Results for a group of detoxified alcoholics are depicted in the following Table 3:

TABLE 3

Pancreatic Antigen (Pan) and Amylase in Sera from Chicago's Alcoholic Treatment Center Patients (n = 29)

| Pan, μg/L | Amylase, U/L | weeks of abstinence | Pan, μg/L | Amylase, U/L | weeks of abstinence |
|---|---|---|---|---|---|
| 8 | 700 | 4 | 2 | 700 | 3 |
| 2 | 910 | 4 | 5 | 600 | 2 |
| 4 | 580 | 4 | 0 | 950 | 3 |
| 7 | 540 | 4 | 4 | 550 | 3 |
| 0 | 730 | 6 | 7 | 970 | 5 |
| 3 | 2180 | 4 | 4 | 1270 | 4 |
| 10 | 620 | 4 | 10 | 1210 | 3 |
| 12 | 840 | 3 | 10 | 880 | 5 |
| 2 | 960 | 5 | 9 | 880 | 5 |
| 3 | 600 | 3 | 3 | 900 | 4 |

TABLE 3-continued

Pancreatic Antigen (Pan) and Amylase
in Sera from Chicago's Alcoholic Treatment
Center Patients (n = 29)

| Pan, μg/L | Amylase, U/L | weeks of abstinence | Pan, μg/L | Amylase, U/L | weeks of abstinence |
|---|---|---|---|---|---|
| 3 | 830 | 4 | 8 | 1090 | 6 |
| 5 | 610 | 4 | 10 | 850 | 4 |
| 5 | 650 | 4 | 9 | 800 | 3 |
| 7 | 1000 | 3 | 6 | 870 | 4 |
| 2 | 750 | — | | | |

The mean value for pancreatic antigen and amylase in serum was 5.5 micrograms per liter and 830 U/L, respectively. In 41% of these subjects (12 cases) pancreatic antigen exceeded 6.0 micrograms per liter (range 7-12).

Although the concept of latent pancreatitis in chronic alcoholics is implied by the findings demonstrated at autopsy and by the pancreatic calcification shown in roentgenograms, these findings represent end-stage disease and provide little help in detecting cases during the early, active phase of the disease. Unfortunately, the asymptomatic (latent) phase of chronic pancreatitis is rarely considered in the literature because it is usually unrecognized, unless punctuated by symptomatic attacks. As a result, little is known as to the state of the pancrease in the absence of, or between, acute attacks of the disease. Because of the general ignorance surrounding the latency of chronic alcoholic pancratitis—which is progressive, once established, even in the face of complete abstinence from alcohol development of a method to detect on-going subclinical pancreatitis is supported by the relevant statistical data cited; that is, differences in the amounts of pancreatic antigen in serum between the control groups (2.1 μg/L) and alcoholic patients (6.7 μg/L) are highly statistically significant by Student's t-test (p 0.0005). The fact that increased amounts of pancreatic antigen are readily demonstrable in 41% of chronic alcoholics three to six weeks after an alcoholic debauch (Table 3) accords with observations from the secretin-pancreozymin stimulation test, in which 54% of asymptomatic chronic alcholics exhibit abnormal pancreatic exocrine function [H. Goebell, et al., "Clinical Asymptomatic Functional Disorders of the Exocrine Pancreas in Chronic Alcoholics," Dtsch. Med. Wochenschr, 95, 808–814, 1970]. Such function tests, however, require special facilities and considerable technical skill, beyond that available in most institutions. In accordance with the present invention, methods are provided for detection of organ specific pancreatic antigen which may be carried out in conventional laboratories. Data relating to the precision of the pancreatic antigen assay are set forth in the following table:

TABLE 4

Precision of the Pancreatic Antigen Assay

| | Pancreatic Antigen Concentration | | |
|---|---|---|---|
| | Low | Medium | High |
| | Interassay | | |
| Mean, μg/L | 2.69 | 9.66 | 23.9 |
| SD, μg/L | 0.31 | 0.56 | 3.7 |
| n | 24 | 24 | 24 |
| CV, % | 11.5 | 5.8 | 15.5 |
| | Intra-Assay | | |
| Mean, μg/L | 2.72 | 9.37 | 25.8 |
| D, μg/L | 0.29 | 0.51 | 1.35 |
| n | 8 | 8 | 8 |

TABLE 4-continued

Precision of the Pancreatic Antigen Assay

| | Pancreatic Antigen Concentration | | |
|---|---|---|---|
| | Low | Medium | High |
| CV, % | 10.6 | 5.4 | 5.23 |

When amylase and pancreatic antigen concentrations in serum from 14 cases of clinically diagnosed acute pancreatitis are compared in the following Table 5, all cases are seen to show increased amounts of the antigen (from 10 to 105 micrograms per liter, but the changes were not proportional to the changes in the amount of amylase:

TABLE 5

Pancreatic Antigen and Amylase in Sera
of 14 Patients Admitted for Acute Pancreatitis

| Amylase, kU/L | Pancreatic antigen, μg/L |
|---|---|
| 28.2 | 105 |
| 50.0 | 52 |
| 50.0 | 50 |
| 47.0 | 62 |
| 50.0 | 42 |
| 7.5 | 22 |
| 3.5 | 47 |
| 2.4 | 35 |
| 13.6 | 30 |
| 12.6 | 30 |
| 9.8 | 25 |
| 3.8 | 20 |
| 0.8 | 15 |
| 1.8 | 10 |

In one case, the amylase concentration was normal, whereas the amount of antigen was increased.

These data support the idea that a significant number of chronic alcholics develop subclinical pancreatic damage early in the course of the disease, that the process continues even during a period of abstinence, and that alcoholic pancreatitis is probably chronic from its inception [K. H. Soergel, supra; W. B. Strum, et al., supra]. Cases exhibiting undoubted clinical signs and symptoms of chronic alcoholic pancreatitis have presumably already incurred permanent pancreatic damage. Finally, although the assay described is largely concerned with the effects of chronic alcoholism, it can facilitate investigation into other causes of pancreatitis, viz, chronic steroid therapy, hyperlipemia and trauma.

In addition to utility in respect to determination of pancreatitis from blood specimens of patients, methods in accordance with the present invention may also be utilized in the determination of pancreatic antigen in primary and metastatic pancreatic carcinoma. In this regard, saline extracts of primary and metastatic pancreatic carcinomas have been tested for their content of (normal) pancreatic antigen (Pan Ag) by the radioimmunoassay procedure described above. The amounts determined were 1000 ng antigen/ml extract for normal pancreas, 700–1300 ng/ml extract for primary pancreatic carcinomas and 500–17,000 ng/ml extract for tumor metastasis to liver, peritoneum and lymph nodes. Detection of normal pancreatic antigen in primary and metastatic tumors of the pancreas may be used for clinical diagnostic analysis of appropriate tissue samples.

Furthermore, while the utility of the present method has been described particularly with respect to radioimmunoassay techniques, various other methods may be utilized. For example, immunofluorescent staining of appropriate substrates may be carried out by conventional procedures utilizing appropriately labelled Pan Ag antigen. For example, fixed cryostat sections may first be incubated with a commercial goat anti-rabbit serum conjugated with FITC (Hyland). For the direct immunofluorescent procedure, the rabbit monospecific antiserum to Pan Ag may be conjugated to FITC by conventional procedures.

Similarly, immunoperoxidase staining techniques may be utilized for determination of Pan Ag in tissue specimens. For example, suitable tissue sections may be incubated with immunoglobulin (obtained from a monospecific antisera to Pan Ag by ammonium sulfate precipitation) for 60 minutes at room temperature. The slides may then be washed with PBS and incubated for 30 minutes with peroxidase-conjugated goat anti-rabbit antiserum (Capel Labs), washed with PBS and incubated for 10 minutes, with fresh diamminobenzidine HCl: $H_2O_2$ to reveal Pan Ag by light or electron microscopy.

Accordingly, it will be appreciated that a pancreas-specific antigen has been isolated and purified, which has valuable application to diagnosis and research in respect to pancreas disease. The Pan Ag may be utilized to provide immunologically pure antibodies reactive with Pan Ag, and which are free of immunologically interfering materials and monospecific to Pan Ag. The Pan Ag specific antibodies may be appropriately labelled by suitable means, such as by radioactive elements, immunofluorescent compounds, or other analytically detectable or reactive compounds such as peroxidase enzymes, to provide quantitative or qualitative analysis for the presence of Pan Ag in a selected tissue or serum sample.

The Pan Ag in accordance with the present invention may be prepared in a form comprising at least about 95 and preferably 99% by weight of the Pan Ag (labeled or unlabeled) excluding biologically inert dilutants or supporting materials).

While the present invention has been described with respect to certain specific embodiments, various adaptations, modifications and variations will become apparent based on the present disclosure, which are intended to be included within the spirit and scope of the following claims.

What is claimed is:

1. Substantially immunologically pure Pan Ag, an isotonic saline soluble pancreatic acinar cell cytoplasmic glycoprotein having a molecular weight of about $2.25 \times 10^5$ daltons, a carbohydrate content of about 18 percent by weight, an antigenic stability in the range of from about pH 2.8 to about 8.5, an antigenic stability to incubation with deoxyribonuclease and ribonuclease, an antigenic instability to incubation with trypsin and neuraminidase and which precipitates at between about 245 and about 340 grams per liter of ammonium sulfate saturation.

2. Pan Ag in accordance with claim 1 which is at least 99 percent by weight pure, exclusive of immunologically inert solvents, diluents or carriers.

3. An immunologically monospecific antibody to the Pan Ag of claim 1.

4. A purified antibody in accordance with claim 3 wherein said antibody is monospecific rabbit immunoglobin G antibody to Pan Ag.

5. A Pan Ag antibody in accordance with claim 3 wherein said antibody is radioactively labelled.

6. A Pan Ag antibody in accordance with claim 3 wherein said antibody is peroxidaselabelled.

7. A Pan Ag antibody in accordance with claim 3 wherein said antibody is labelled with a fluorescent dye.

8. A method for detecting the presence of Pan Ag in a biological sample, comprising the steps of contacting the sample with a monospecific antibody for Pan Ag, and detecting the Pan Ag-antibody reaction product.

9. A method in accordance with claim 8 wherein said reaction product is detected and quantified by radioimmunoassay, immunofluorescent or immunoperoxidase technique.

10. Pan Ag in accordance with claim 1, which is radioactively labelled.

11. Radioactively labelled Pan Ag in accordance with claim 10, which is complexed with an antibody for Pan Ag.

12. A method for detecting the presence of Pan Ag in a biological sample, comprising the steps of contacting the sample with a labelled complex of a Pan Ag as claimed in claim 1 and a monospecific antibody for said Pan Ag, and measuring the amount of labelled Pan Ag released by contact with said sample.

13. A method for providing a monospecific Pan Ag antiserum comprising the steps of percutaneously applying substantially immunologically pure Pan Ag antigen as claimed in claim 1 to a suitable mammal, collecting serum from said mammal after antibody development therein, and absorbing said animal serum or insolubilized normal human serum to provide a monospecific animal antiserum (antibody) to human pancreatic antigen.

14. A method for preparing and isolating Pan Ag, cytoplasmic pancreatic acinar cell protein, comprising the steps of preparing an aqueous saline (9 grams per liter NaCl) extract of human pancreas, dialyzing the saline extract against distilled water, and subsequently dialyzing against tris(hydroxymethyl) methylamine(Tris)-glycine buffer (pH 9.1, 0.04 mol/liter) to provide a dialyzed extract, centrifuging the dialyzed extract at $27,000 \times g$ for 20 minutes, collecting the supernate, fractionating the supernate by preparative polyacrylamide gel gradient electrophoresis to provide 14 principal protein bands, providing a mammal antiserum to the seventh protein band contacting the mammal antiserum with polymerized normal human serum, to produce an antiserum specific for pancreas and polymerizing the pancreasspecific antiserum with gluteraldehyde to form an insoluble immunoabsorbant, preparing an aqueous saline (9 grams per liter NaCl) extract of human pancreas, heating the extract to 60° C., immediately cooling the heated extract to 4° C., centrifuging the cooled extract at $27,000 \times g$ for 20 minutes at 4° C., dialyzing the centrifugation supernate against 0.05 mol/liter sodium phosphate buffer (pH 6.0), centrifuging the dialyzed supernate at $27,000 \times g$, filtering the dialyzed centrifugation supernate, mixing the filtered dialyzed centrifugation supernate with carboxymethyl dextran polymer gel, washing the gel with 0.05 mol/liter sodium phosphate buffer (pH 6.0), eluting adsorbed pancreatic proteins from the carboxymethyl dextran polymer gel to provide a protein solution, selectively absorbing components having a molecular weight of less than about 200,000 by subjecting said protein solution to gel filtration while passing through higher molecular weight components having molecular weight of more than about 200,000 in the gel filtration void volume, and collecting the gel filtration void volume solution,     subjecting the gel filtration void volume solution to preparative polyacrylamide gel electrophoresis in glycine buffer at pH of about 9.2 to separate the components into six principal proteins bands,     fractionating the third electrophoretically separated band (from the cathode) by immunoaffinity chromatography by contacting the protein with said insoluble immunoabsorbant to separate the pancreas-specific component from the non-absorbed components, eluting the pancreatic antigen (Pan Ag) from the insoluble immunoabsorbant, and subjecting the Pan Ag eluted from said insoluble immunoabsorbant to polyacrylamide disk gel electrophoresis to detect a single protein band, indicating a substantially pure pancreatic antigen containing about 18 percent by weight carbohydrate as determined by the phenolsulfuric acid method, which retains its antigenic activity in a pH range of from about 2.8 to about 8.5, but which is destroyed at pH 2.5, which is stable to incubation with deoxyribonuclease and ribonuclease, and which has a mass of about $2.25 \times 10^5$ daltons as determined by polyacrylamide gel filtration versus IgE, follitropin, insulin, carcinoembryonic antigen and dextran reference markers.

15. The pancreatic antigen (Pan Ag) prepared by the method of claim 14.

16. A labelled immunologically monospecific antibody to the Pan Ag of claim 15.

17. A method in accordance with claim 8 for testing for an abnormal pancreatic condition in which the sample is a human blood sample and wherein the method further comprises determining whether the sample contains in excess of a predetermined quantity of Pan Ag in the range of from about 6 to about 10 micrograms per liter of Pan Ag.

18. A monospecific antibody in accordance with claim 8 which is immunologically unreactive toward the pancreatic proteins insulin, amylase, lipase, elastase, carboxypeptidase A, carboxypeptidase B, collagenase, leucine, aminopeptidase, phospholipase, carbonic anhydrase and gammaglutamyltransferase.

* * * * *